(12) United States Patent
Lim et al.

(10) Patent No.: US 9,822,084 B2
(45) Date of Patent: Nov. 21, 2017

(54) METHOD FOR PREPARING CALCOBUTROL

(71) Applicant: ST PHARM CO., LTD., Gyeonggi-do (KR)

(72) Inventors: Geun Jho Lim, Gyeonggi-do (KR); Sun Ki Chang, Gyeonggi-do (KR); Chang Ho Byeon, Gyeonggi-do (KR); Hoe Jin Yoon, Gyeonggi-do (KR); Moon Soo Kim, Gyeonggi-do (KR)

(73) Assignee: ST PHARM CO., LTD., Gyeonggi-do (KR)

( * ) Notice: Subject to any disclaimer, the term of this patent is extended or adjusted under 35 U.S.C. 154(b) by 0 days.

(21) Appl. No.: 15/511,882

(22) PCT Filed: Sep. 7, 2015

(86) PCT No.: PCT/KR2015/009413
§ 371 (c)(1),
(2) Date: Mar. 16, 2017

(87) PCT Pub. No.: WO2016/043462
PCT Pub. Date: Mar. 24, 2016

(65) Prior Publication Data
US 2017/0260148 A1    Sep. 14, 2017

(30) Foreign Application Priority Data
Sep. 17, 2014 (KR) .................. 10-2014-0123532

(51) Int. Cl.
*C07D 257/02* (2006.01)

(52) U.S. Cl.
CPC .................. *C07D 257/02* (2013.01)

(58) Field of Classification Search
CPC .................................... C07D 257/02
See application file for complete search history.

(56) References Cited

FOREIGN PATENT DOCUMENTS

| KR | 100269081 B1 | 10/2000 |
| KR | 1020110058746 A | 6/2011 |
| KR | 1020140035911 A | 3/2014 |
| KR | 1020140097411 A | 8/2014 |

OTHER PUBLICATIONS

Platzek, J., "Synthesis and structure of a new macrocyclic polyhydroxylated gadolinium chelate used as a contrast agent for magnetic resonance imaging." Inorganic chemistry 36.26 (1997): 6086-6093.*
Platzek, J. et al., "Synthesis and Structure of a New Macrocyclic Polyhydroxylated Gadolinium Chelate Used as a Contrast Agent for Magnetic Resonance Imaging", Inorganic Chemistry (1997), pp. 6086-6093, vol. 36, issue 26, American Chemical Society, Copyright 1997.

* cited by examiner

*Primary Examiner* — John M Mauro
(74) *Attorney, Agent, or Firm* — Avery N. Goldstein; Blue Filament Law PLLC

(57) ABSTRACT

Disclosed is a novel method of preparing highly pure calcobutrol using an intermediate (butrol) of gadobutrol without using highly pure gadobutrol. This method is capable of obtaining calcobutrol at high purity and high yield through a simple and environmentally friendly process, and thus can be easily applied to mass production.

15 Claims, No Drawings

METHOD FOR PREPARING CALCOBUTROL

TECHNICAL FIELD

The present invention relates to a novel method of preparing calcobutrol. Particularly, the present invention relates to a method of preparing highly pure calcobutrol through a simple process.

BACKGROUND ART

In the field of gadolinium-containing contrast agents, gadobutrol is commercially available under the trade name of Gadovist or Gadavist all over the world.

Gadobutrol is a nonionic complex of gadolinium (III) and a macrocyclic ligand 10-(2,3-dihydroxy-1-(hydroxymethyl) propyl)-1,4,7,10-tetraazacyclododecane-1,4,7-triacetic acid (butrol), and functions to shorten the relaxation time of protons in tissue water at clinically recommended doses.

However, in most gadolinium-containing contrast agents, including gadobutrol, it has come to be known that the use of an excess of complex-forming ligand therein in the form of a calcium complex is favorable. The calcium complex plays a role in preventing the release of free gadolinium from, the formulation (e.g. by storage for many years through re-complexation with foreign ions derived from glass).

Calcobutrol, represented by Chemical Formula 1 below, is a complex of calcium and 10-(2,3-dihydroxy-1-(hydroxymethyl)propyl)-1,4,7,10-tetraazacyclododecane-1,4,7-triacetic acid (butrol), and is able to prevent the release of free gadolinium from gadobutrol, thus solving the problem of toxicity of gadolinium ions, and is contained as an additive (calcobutrol sodium salt) in Gadovist.

[Chemical Formula 1]

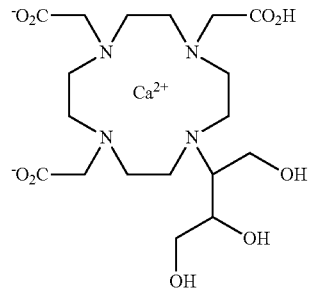

The synthesis of calcobutrol is described in detail in the literature (Inorg. Chem. 1997, 36, 6086-6093). However, the process disclosed in the above literature does not provide calcobutrol having high purity. When faithfully reproducing the process of Scheme 3 of the above literature, a material having a purity of about 90% through HPLC (stationary phase: Hypersil phenyl (5 μm) of SHANDON; mobile phase: acetonitrile/borate buffer (pH 8) (volume ratio 20/100); detection: UV detector (200 nm); injection volume: 10 μL) is obtained.

Meanwhile, a ligand (butrol) obtainable during the synthesis route of gadobutrol cannot be purified through crystallization, making it impossible to attain the high purity necessary for directly transferring it to a calcium complex. A neutral gadolinium complex, namely gadobutrol, may be obtained at very high purity (>99.7%) through very effective crystallization following purification in an ion exchange column after the reaction of butrol and gadolinium. However, calcobutrol is not easy to purify because of the extra acid functionality. Hence, the route for directly preparing calcobutrol from butrol is considered unsuitable in terms of purity.

With the goal of solving the above problem, Korean Patent Application Publication No. 2011-0058746 discloses a method of preparing highly pure calcobutrol, comprising decomplexing already-obtained gadobutrol, serving as a starting material, removing gadolinium ions to give butrol, and then complexing the butrol with calcium. However, the method of the above patent is problematic because gadobutrol is used as an intermediate in the synthesis of calcobutrol, thus negating economic benefits and complicating the preparation process.

Accordingly, it is required to develop a novel method of preparing highly pure calcobutrol at a high yield through simple, economic and mild preparation processing.

DISCLOSURE

Technical Problem

Accordingly, the present invention is intended to provide a method of preparing calcobutrol, which is simple compared to existing calcobutrol synthesis methods including preparing highly pure gadobutrol and then removing gadolinium ions from the gadobutrol, and is economical and mild because calcobutrol may be obtained at high purity compared to when using an intermediate of gadobutrol.

Technical Solution

In order to accomplish the object of the present disclosure, the present disclosure provides a novel method for preparing calcobutrol.

The method of the present disclosure comprises: (S1) preparing a compound of Formula 3 below by using a compound of Formula 2 below or its salt; (S2) preparing a compound of Formula 4 below by using the compound of Formula 3; and (S3) preparing a compound of Formula 1 below by using the compound of Formula 4.

[Formula 1]

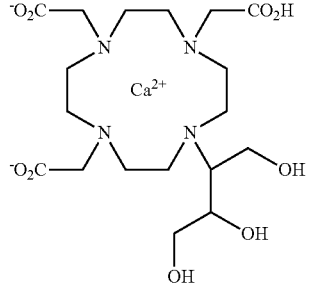

[Formula 2]

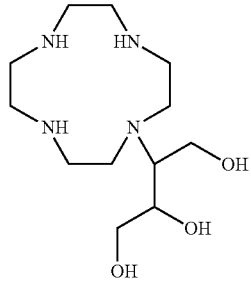

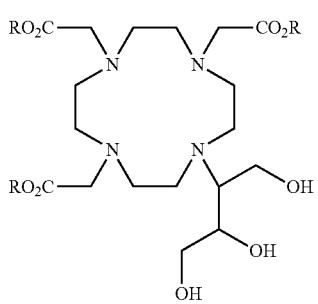

[Formula 3]

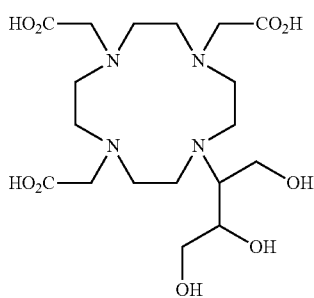

[Formula 4]

{Wherein, R is linear or branched-chain alkyl of $C_1$-$C_4$}

Each step will be described more fully hereinafter.

(S1): Carboxymethylation

Apropos of the preparation method of the present disclosure, the (S1) step relates to a preparation of the compound of Formula 3 by reacting (i.e. carboxymethylating) the compound of Formula 2 or its salt with a compound of Formula 5 below.

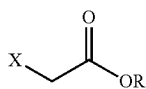

[Formula 5]

{Wherein, R is linear or branched-chain alkyl of $C_1$-$C_4$ and X is halogen, TsO⁻ or MsO⁻}

In some embodiment of the present disclosure, the compound of Formula 2 or its salt in the (S1) step can be 4 hydrochloride of Formula 6 below.

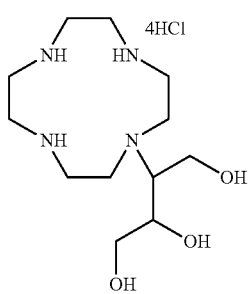

[Formula 6]

Also, in some embodiment of the present disclosure, the compound of Formula 3 in the (S1) step can be a compound of Formula 7 below wherein R is t-Butyl.

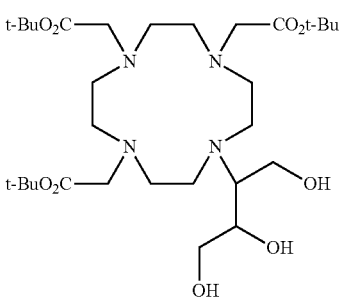

[Formula 7]

Also, in some embodiment of the present disclosure, the compound of Formula 5 can be a compound of Formula 8 below wherein X is Br and R is t-Butyl.

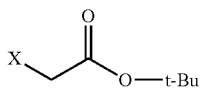

[Formula 8]

In the (S1) step, the reaction can be performed under the existence of an organic solvent which is commonly used for alkylation (i.e. carboxymethylation) reaction. Preferably, the organic solvent can be a mixed solvent of water and $C_4$-$C_{11}$ ether, and more preferably the organic solvent can be a mixed solvent of water and tetrahydrofuran (THF), but not limited to the above.

Also, the reaction can be performed under the existence of a base, specifically under the existence of an inorganic base. Preferably, the base can be a weak base such as potassium carbonate ($K_2CO_3$), sodium bicarbonate ($NaHCO_3$), potassium bicarbonate ($KHCO_3$) or of mixtures thereof, and more preferably the base can be potassium carbonate but not limited to the above.

The reaction in the (S1) step can be performed at 50 to 80° C., preferably at 65 to 70° C. and more preferably at 63 to 68° C. but not limited to the above.

According to some embodiment of the present disclosure, the (S1) step can further comprise a crystallization process of the compound of Formula 3.

A crystallization solvent used in the crystallization process can be methylene chloride, $C_4$-$C_{11}$ ether, $C_4$-$C_8$ alkane or mixtures thereof, and it is preferable to use a mixture of methylene chloride and n-Hexane.

The compound of Formula 3 can be yielded in high-purity of 99% or more, preferably 99.5% or more, and more preferably 99.7% or more through (S1).

(S2): Acid Hydrolysis

In the preparation method according to the present invention, step (S2) is preparing the compound (butrol) of Chemical Formula 4 to high purity by subjecting the compound having high purity of Chemical Formula 3 to acid hydrolysis.

The acid hydrolysis can be performed by using common reaction condition for acid hydrolysis of ester compound. Preferably, the acid hydrolysis can be performed by adding dilute hydrochloric acid solution or dilute sulfuric acid solution to the compound of Formula 3.

Also, the acid hydrolysis can be performed at 50 to 70° C., preferably at 55 to 65° C. and more preferably at 57 to 63° C., but not limited to the above.

In some embodiment of the present disclosure, the (S2) step can comprises a purification process of the compound of Formula 4 by using resin.

Additionally, according to the some embodiment of the present disclosure, the (S2) step can further comprise a crystallization process.

A solvent used in the crystallization process can be methanol, acetone or mixtures thereof, and it is preferable to use a mixed solvent of methanol and acetone.

The compound of Formula 4 (butrol) can be yielded in high-purity of 90% or more, preferably 95% or more, and more preferably 98% or more through (S2).

Step (S3): Formation of Calcium Complex

Apropos of the preparation method of the present disclosure, the (S3) step relates to a preparation of calcobutrol that is a calcium complex by reacting the compound (butrol) of Formula 4 prepared in high-purity in the (S2) step with a calcium ion source.

The calcium ion source may include any type of compound able to supply calcium ions, and preferably includes, but is not limited to, calcium carbonate, calcium chloride, calcium oxalate, calcium phosphate, or calcium hydroxide.

The reaction in the (S3) step can be performed at 80 to 100° C., preferably at 85 to 95° C., and more preferably at 87 to 93° C. but not limited to the above.

The (S3) step can further comprise a crystallization process of calcobutrol.

The compound of Formula 1 (calcobutrol) can be yielded in high-purity of 99% or more, preferably 99.5% or more, and more preferably 99.9% or more through the (S3) step.

In some embodiment of the present disclosure, calcobutrol can be prepared through a method represented by Scheme 1 below.

[Scheme 1]

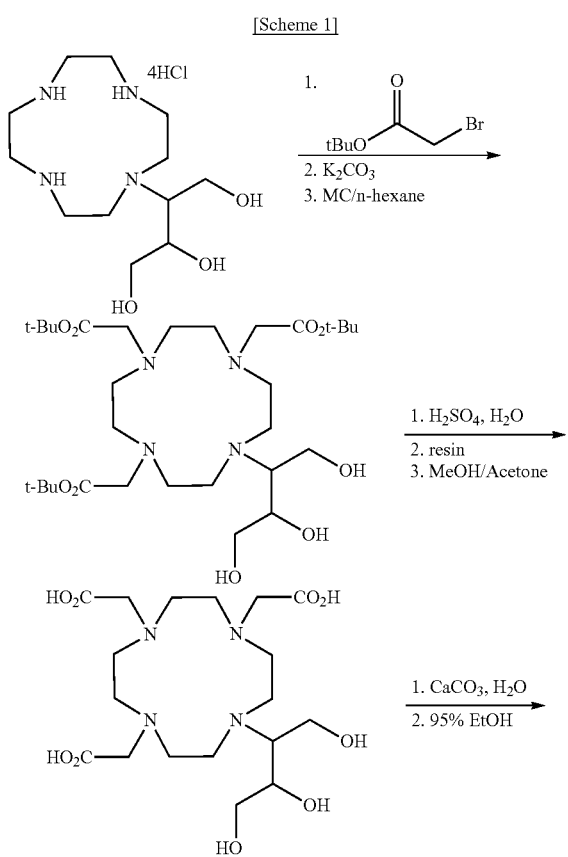

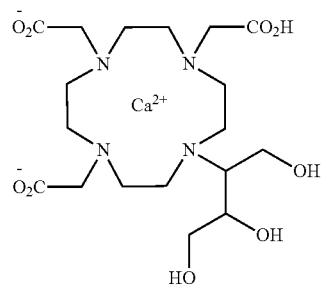

Advantageous Effects

According to the present invention, the preparation method does not contain gadobutrol in the reaction route, unlike existing gadobutrol synthesis methods, thus obviating the need to handle gadolinium, which is toxic, and the reaction processing is very mild.

Also, the preparation method of the present invention is capable of obtaining calcobutrol at high purity through only a simple process, unlike existing synthesis methods, and is thus suitable for mass production.

BEST MODE

The present disclosure will be described more fully hereinafter with reference to the accompanying examples. However, the present disclosure may be embodied in many different forms, and should not be construed as being limited to the examples set forth herein.

In addition, reagents and solvents disclosed hereinafter were purchased from Sigma-Aldrich Korea unless otherwise said, IR was measured by using Jasco's FT-IR 4100 series; HPLC was measured by using Agilent Technoliges' 1200 Series; and $^1$H NMR was measured by using Varian Mercury Instrument's Oxford NMR 300 MHz Spectrometer. Purity was calculated as area % of HPLC.

EXAMPLE 1

Step 1: Preparation of tert-butyl-2,2',2''-(10-(1,3,4-trihydroxybutan-2-yl)-1,4,7,10-tetraazacyclododecan-1,4,7-triyl)triacetate 3-(1,4,7,10-tetraazacyclododecan-1-yl)butan-1,2,4-triol 4 hydrochloride (100 g, 0.2368 mol) was dissolved under stirring in 500 ml of purified water and 1500 ml of tetrahydrofuran. Potassium carbonate (327 g, 2.3684 mol) was added thereto at room temperature and Cert-butyl bromoacetate (143.2 g, 0.434 mmol) was slowly added thereto. Upon completion of the addition, a reaction was performed at 63 to 68° C. When the reaction was terminated, 1000 ml of purified water was added thereto and stirred, and then an aqueous layer was separated. The solvent of separated organic layer was removed by concentrating under reduced pressure and then an organic layer was separated by using 1500 ml of purified water and 1000 ml of toluene. An aqueous layer was separated by adding 550 ml of hydrochloric acid to the separated organic layer. 500 ml of methylene chloride was added to the separated aqueous layer and pH was adjusted to 9.3 to 9.8 by using 100 g of sodium carbonate, and then an organic layer was separated therefrom. The separated organic layer was washed with 10% salt water to separate the organic layer and dehydration was performed, and then the solvent was concentrated under reduced pressure. 400 ml of methylene chloride and 1600 ml of n-hexane were added to the concentrated residue and the resulting solid therefrom was filtered and dried to prepare 117.3 g of tert-butyl-2,2',2"-(10-(1,3,4-trihydroxybutan-2-yl)-1,4,7,10-tetraazacyclododecan-1,4,7-triyl)triacetate.

Yield: 80%, Purity: 99.7%

$^1$H-NMR (CDCl$_3$, 300 MHz): δ (ppm) 1.46 (s, 9H), 1.90~3.10 (m, 11H), 3.20~3.80 (m, 17H)

Infrared spectrum(KBr, cm$^{-1}$): 3350, 2980, 2960, 2860, 2820, 1730, 1455

Step 2: Preparation of 2,2',2"-(10-(1,3,4-trihydroxybutan-2-yl)-1,4,7,10-tetraazacyclododecan-1,4,7-triyl)triacetic acid (butrol)

Internal temperature was raised to 57~63° C. while tert-butyl-2,2',2"-(10-(1,3,4-trihydroxybutan-2-yl)-1,4,7,10-tetraazacyclododecan-1,4,7-triyl)triacetate (30 g, 0.048 mol) prepared in Step 1 was dissolved under stirring in 60 ml of purified water. After elevating the temperature, a mixed solution of 60 ml of purified water and 6 ml of sulfuric acid prepared in advance was added drop-wise. A reaction was performed for 4 hours at the same temperature and cooled to room temperature (20 to 25° C.) upon confirming termination of the reaction. When the cooling was completed, the same was treated with resin (5 v/w) and concentrated. 90 ml of methanol and 300 ml of acetone were added to the concentrated residue and resulting crystal was washed with acetone. The filtered crystal was dried in vacuo at internal temperature of 50° C. to prepare 20.1 g of 2,2',2"-(10-(1,3,4-trihydroxybutan-2-yl)-1,4,7,10-tetraazacyclododecan-1,4,7-triyl)triacetic acid.

Yield: 92%, Purity: 98%

$^1$H-NMR(CDCl$_3$, 300 MHz): δ (ppm) 1.92~3.15 (m, 11H), 3.23~3.88 (m, 17H)

Infrared spectrum(KBr, cm$^{-1}$): 3350, 2980, 2960, 2860, 2820, 1730, 1455

Step 3: Preparation of 10-(2,3-dihydroxy-1(hydroxymethyl)propyl)-1,4,7,10-tetraazacyclododecane-1,4,7-triacetic acid-calcium complex (calcobutrol)

2,2',2"-(10-(1,3,4-trihydroxybutan-2-yl)-1,4,7,10-tetraazacyclododecane-1,4,7-triyl)triacetic acid (15.4 g, 0.0342 mol), prepared in step 2, was dissolved in 154 ml of purified water with stirring and then added with calcium carbonate (3.42 g, 0.0335 mol). The internal temperature was increased to 87~93° C. and the mixture was stirred at the same temperature for 1 hr. After the termination of the reaction, the reaction solution was filtered using diatomaceous earth, and the filtrate was concentrated under reduced pressure. The concentrated residue was added with 231 ml of ethanol and refluxed with stirring. The resulting product was cooled to room temperature (20~25° C.), stirred at the same temperature for 1 hr, and filtered in a nitrogen atmosphere. The filtered crystal was dried in a vacuum at an internal temperature of 50° C. or less, thus obtaining 13.0 g of a 10-(2,3-dihydroxy-1(hydroxymethyl)propyl)-1,4,7,10-tetraazacyclododecane-1,4,7-triacetic acid-calcium complex.

Yield 74.3%, Purity 99.5%

$^1$H-NMR (DMSO, d$_6$): δ (ppm) 1.90~2.30 (m), 2.40~2.90 (m), 3.0~3.80 (m), 3.91 (d)

Infrared spectrum (KBr, cm$^{-1}$): 3400, 2960, 2840, 1600, 1410, 1290, 1275

EXAMPLE 2

2,2',2"-(10-(1,3,4-trihydroxybutan-2-yl)-1,4,7,10-tetraazacyclododecane-1,4,7-triyl)triacetic acid (18.0 g, 0.0399 mol), prepared in step 2 of Example 1, was dissolved in 144 ml of purified water with stirring, and then added with calcium carbonate (4.00 g, 0.0399 mol). The internal temperature was increased to 87~93° C. and the mixture was stirred at the same temperature for 1 hr. After the termination of the reaction, the reaction solution was filtered using diatomaceous earth, and the filtrate was concentrated under reduced pressure. The concentrated residue was added with 180 ml of ethanol and 180 ml of acetone and refluxed with stirring. The resulting product was cooled to 0~5° C., stirred at the same temperature for 1 hr, and filtered in a nitrogen atmosphere. The filtered crystal was dried in a vacuum at an internal temperature of 50° C. or less, thus obtaining 13.0 g of a 10-(2,3-dihydroxy-1(hydroxymethyl)propyl)-1,4,7,10-tetraazacyclododecane-1,4,7-triacetic acid-calcium complex.

Yield 62.9%, Purity 99.4%

$^1$H-NMR (DMSO, d$_6$): δ (ppm) 1.90~2.30 (m), 2.40~2.90 (m), 3.0~3.80 (m), 3.91 (d)

Infrared spectrum (KBr, cm$^{-1}$): 3400, 2960, 2840, 1600, 1410, 1290, 1275

INDUSTRIAL APPLICABILITY

The preparation process of the present disclosure is very adequate for a large scale production because the process is very mild and high-purity calcobutrol can be prepared by simple process.

The invention claimed is:

1. A method for preparing a compound of Formula 1 (calcobutrol) comprising:
    (S1) preparing a compound of Formula 3 from a compound of Formula 2 or a salt thereof;
    (S2) preparing a compound of Formula 4 from the compound of Formula 3; and
    (S3) preparing a compound of Formula 1 from the compound of Formula 4

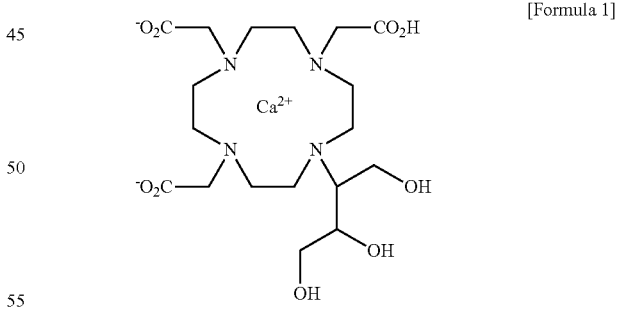

[Formula 1]

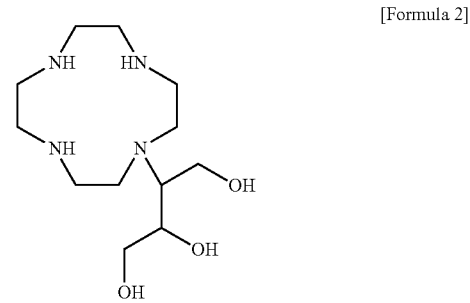 [SMILES: OCC(O)C(CO)N1CCNCCNCCNCC1]

[Formula 2]

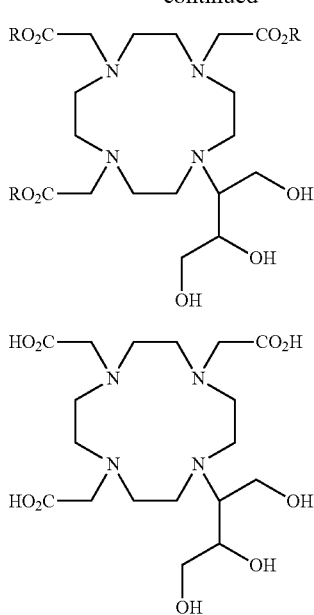

[Formula 3]

[Formula 4]

wherein R is a linear or branched-chain $C_1$-$C_4$ alkyl group.

2. The method according to claim 1, wherein the (S1) step comprises reacting the compound of Formula 2 with a compound of Formula 5 in a solvent consisting of water, a $C_4$-$C_{11}$ ether and an inorganic base

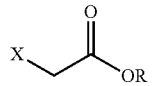

[Formula 5]

wherein R is as defined in claim 1 and X is halogen, tosylate or mesylate.

3. The method according to claim 2, wherein the ether is tetrahydrofuran (THF).

4. The method according to claim 2, wherein the inorganic base is potassium carbonate ($K_2CO_3$), sodium bicarbonate ($NaHCO_3$), potassium bicarbonate ($KHCO_3$) or a mixture thereof.

5. The method according to claim 2, wherein the (S1) step further comprises crystallization of the compound of Formula 3.

6. The method according to claim 5, wherein a crystallization solvent used in the crystallization is methylene chloride, $C_4$-$C_{11}$ ether, $C_4$-$C_8$ alkane or a mixture thereof.

7. The method according to claim 6, wherein the crystallization solvent is a mixture of methylene chloride and n-hexane.

8. The method according to claim 1, wherein the salt of the compound of Formula 2 in the (S1) step is the hydrochloride of Formula 6

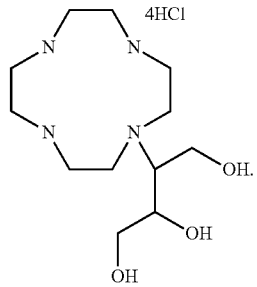

[Formula 6]

9. The method according claim 1, wherein the compound of Formula 3 in the (S1) step is a compound of Formula 7

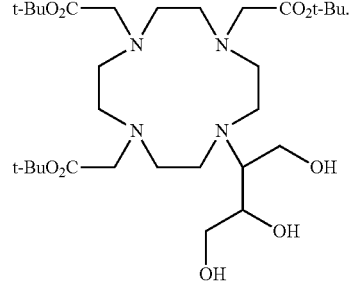

[Formula 7]

10. The method according to claim 1, wherein the (S2) step comprises an acid hydrolysis.

11. The method according to claim 10, wherein the (S2) step further comprises purification of the compound of Formula 4 using resin.

12. The method according to claim 11, wherein the (S2) step further comprises crystallization of the compound of Formula 4.

13. The method according to claim 12, wherein a solvent used in the crystallization is methanol, acetone or a mixture thereof.

14. The method of claim 1, wherein the step (S3) comprises reacting the compound of Formula 4 with a calcium ion source.

15. The method of claim 14, wherein the calcium ion source is calcium carbonate, calcium chloride, calcium oxalate, calcium phosphate, or calcium hydroxide.

* * * * *